United States Patent [19]

Dietz

[11] Patent Number: 5,074,299

[45] Date of Patent: * Dec. 24, 1991

[54] MONITOR FOR CONTROLLING THE FLOW OF GASES FOR BREATHING DURING INHALATION

[76] Inventor: Henry G. Dietz, 80 Salisbury Ave., Garden City, N.Y. 11530

[*] Notice: The portion of the term of this patent subsequent to May 24, 2005 has been disclaimed.

[21] Appl. No.: 402,680

[22] Filed: Sep. 5, 1989

Related U.S. Application Data

[63] Continuation of Ser. No. 189,397, May 2, 1988, abandoned.

[51] Int. Cl.[5] .............................................. A61M 16/00
[52] U.S. Cl. ........................... 128/204.21; 128/204.23; 128/204.26
[58] Field of Search ..................... 128/204.18, 204.21, 128/204.23, 204.26, 205.22, 205.23, 205.24, 716, 721; 73/705, 861.42

[56] References Cited

U.S. PATENT DOCUMENTS

| | | | |
|---|---|---|---|
| 4,360,247 | 11/1982 | Beasley | 73/705 |
| 4,602,643 | 7/1986 | Dietz | 128/721 |
| 4,744,356 | 5/1988 | Greenwood | 128/204.26 |
| 4,745,925 | 5/1988 | Dietz | 73/705 |

Primary Examiner—Aaron J. Lewis

[57] ABSTRACT

A monitor for controlling the flow of respiratory gases to only occur and be maintained as long as a human user of the monitor inhales. The monitor can function by sensing inhalation or exhalation by either use of a nasal cannula or a pneumatic breathing belt that detects body movements due to breating by the human user.

10 Claims, 7 Drawing Sheets

MONITOR FOR CONTROLLING THE FLOW OF GASES FOR BREATHING DURING INHALATION

This is a continuation of application Ser. No. 07/189,397, filed May 2, 1988 now abandoned.

BACKGROUND OF THE INVENTION

This invention relates generally to breathing apparatus and more particularly to controlling the supply of a flow of respiratory treatment gases to a human being as an intermittent gas flow that results in no gas flow during exhalation by the user.

Breathing apparatus in which gas flow is triggered by a human user's spontaneous demand are known. The known apparatus require inhalation to be sensed by a mouth piece or by a tight fitting mask that fits over the mouth and nose to prevent loss of the sensing of inhalation negative pressure. In an attempt to find a more comfortable means to detect inhalation, nasal cannulas have been employed both to sense inhalation and to deliver respiratory gases.

The use of nasal cannula for such dual purposes makes it possible to determine the on-set of inspiration to trigger delivery of a specific dose of a respiratory gas. It is impossible to determine the dose of respiratory gas as a function of the time of inspiration, because it is impossible to both sense and deliver the respiratory gas at the same time when the cannula is used for a dual purpose. The supplying of a large fixed dose of respiratory gas at an early stage of inspiration overlooks the fact that the breathing of a human being is subject to spontaneous changes, and that breathing is a rhythmical act controlled by special control centers in the human brain stem. The rate and depth of breathing are principally controlled by the oxygen and carbon dioxide levels in the arterial blood acting through a classical feedback loop. A fixed dose of respiratory gas cannot provide for the requirements of a human being since the rate of breathing is subject to spontaneous change due to sleeping, exercising, etc. and, therefore, such a method is not satisfactory.

The use of a nasal cannula has a number of other disadvantages when used for both sensing inhalation and delivering of the respiratory gas:

A—The nasal cannula cannot sense inhalation when a human being breaths through his mouth, which often occurs during sleep or when the air passageways in the nose are not open.

B—The nasal cannula cannot be used with humidifiers when it is delivering a respiratory gas, since it is possible for sufficient moisture to accumulate in the supply tubing making it impossible to sense inhalation by the same tube.

If a breathing apparatus is required for such use as oxygen therapy, it is necessary that it function during periods of sleep. Studies reveal that patients receiving oxygen for at least 15 hours per day have almost a 50% better survival rate than those having no supplemental oxygen when such patients have advanced bronchitis or emphysema with defined abnormal airway function and stable partial pressure for oxygen in alveolar gas of less than 60 mm Hg. (Oxygen Therapy - P. Howard).

The present invention overcomes these disadvantages by separating the sensing function from the delivery of the respiratory gas function.

Sensing of inhalation can be accomplished by the Dietz invention by selecting one of two ways, the first is by using a "Pneumatic Breathing Belt Sensor With Minimum Space Maintaining Tapes" (Dietz U.S. Pat. No. 4,602,643 of July 29, 1986). This pneumatic breathing belt sensor detects the expansion and contraction of the chest, abdomen, side or back, by pneumatic means. Expansion of the chest is changed into a positive flow of air (pressure) when inhalation takes place. Contraction of the chest is changed into a negative flow of air (vacuum) when exhalation takes place. The sensor, in the form of a belt with minimum space-maintaining tapes, is worn by the human user and is connected to an appropriate monitor by means of tubing.

The minimum space-maintaining tapes allows the human freedom of movement and prevents such body movements from affecting the operation of the sensor. On inspiration, a dome-shaped diaphragm contracts, the adbominal contents are forced down and forward, and the rib cage is lifted. Both increase the volume of the thorax (or chest).

Respiratory gas is made to flow each time there is a positive pressure flowing from the pneumatic breathing belt, which occurs whenever inhalation is taking place, which results in an increased volume and expansion of the chest.

The second way the present invention can sense inhalation is by means of a two prong nasal cannula. One prong is used for delivery of the respiratory gas and the second prong is used for sensing inhalation.

This method of sensing can be used as an alternate method when the human being is fully aware and capable of determining if breathing through the nose is taking place, and does not wish to wear the pneumatic breathing belt for certain activities.

However, it has the disadvantage that if the wearer falls asleep and breaths through the mouth, the sensor will not function.

The positive flow of air of the pneumatic breathing belt can be detected by using an optoelectronic inhalation sensor (Dietz patent application Ser. No. 06/916,660 Filed Oct. 6, 1986, for which a Notice of Allowance has been issued) as a differential pressure switch to measure the flow of air by use of an orifice to obtain differential pressure.

This optoelectronic inhalation sensor contained in the breathing apparatus can also be used to detect the negative pressure of the one prong (used for sensing) of the two prong nasal cannula when inhalation takes place.

The preferred embodiment is to use the optoelectronic inhalation sensor. However, a Microbridge Mass Airflow Sensor, such as the AWM2100V manufactured by the Micro Switch Division of Honeywell can be used to detect the positive air flow of the pneumatic breathing belt or the negative pressure of the one sensing prong of the two prong nasal cannula when inhalation takes place. The advantage of using the optoelectronic inhalation sensor is that the Microbridge Mass Airflow Sensor is more affected by moisture, and requires a filter to be used in line which reduces its sensitivity. It also requires a higher voltage dual power supply, and higher power requirements that results in shorter battery life of portable equipment.

Since the respiratory gas supply is separate from the sensing means, there is no possibility of feedback between the two, and non-detection of apnea by the sensor can not occur due to parasitic oscillations.

The breathing apparatus supply of respiratory gas can be delivered with simple nasal cannula for daytime use and with a loose fitting mouth nose mask for night-time use when the human is sleeping.

Where the breathing apparatus is used in industrial applications, it is possible to supply a controlled high rate of flow of respiratory air for breathing and a lower continuous rate of flow to assure that a hood or mask is always at a positive pressure to flush out contaminants from being breathed in from the outside environment when the pneumatic breathing belt is used.

The prior art (U.S. Pat. No. 3,400,713), in using belts to detect respiration, has considerable delay between the movement of the chest and the operation of the valve controlling the flow of respiratory gas as such devices are completely mechanical and did not use modern electronic methods.

The Dietz invention overcomes this problem due to the extreme sensitivity of the Optoelectronic Inhalation Sensor which is actuated by pressures as low as 0.001 of an ounce per square inch. The valve is operated by an outside source of energy and not dependent on belt pressure to perform the valving function.

The pneumatic breathing belt with minimum space-maintaining tapes, makes the use of a belt practical because it allows freedom of movement and prevents body movements from affecting the operation of the sensor.

SUMMARY OF THE INVENTION

A breathing apparatus including means for sensing either time of inspiration or time of expiration for each breath, connected to a monitor that sends a signal to a solenoid operated valve that is actuated to prevent a continuous flow of respiratory gas supply from flowing during exhalation. In the preferred embodiment, the sensing means is a pneumatic belt that detects expansion and contraction of the chest as positive or negative flow of air. This flow of air actuates a differential pressure switch (that can be actuated by pressure or a vacuum of 0.001 ounce per square inch) or a flow switch, which is connected to a normally open solenoid operated valve. The valve is actuated during exhalation to stop the flow of respiratory gas from the supply source. The supply source can be from a tank, supply line, compressor, oxygen concentrator, or liquid oxygen. Usual practice is to fill tanks to have a pressure of 2,000 pounds per square inch. A fixed pressure regulator is used to lower this tank pressure to 20/50 pounds per square inch as is normally available from low pressure supply lines.

The fixed lower pressure of 20/50 pounds per square inch is connected to a second adjustable regulator that is capable of zero pressure regulation. A flowmeter is connected to the second adjustable regulator so that the rate of flow can be adjusted to give the required liters per minute of respiratory gas flow supply. This gas supply is connected to the normally open solenoid operated valve that shuts off the flow of respiratory gas each time exhalation by the human user takes place.

An alarm is provided which indicates if the human user stops breathing or the sensor becomes inoperative. This is accomplished by using a missing pulse detector that will operate an alarm if the detector fails to receive incoming signals from the sensor for some fixed period, such as 30 seconds. This alarm can be manually reset or disconnected.

A low battery voltage indicator illuminates a light emitting diode if the battery needs recharging.

The breathing apparatus can also be operated from an alternating power outlet or battery. A rechargeable battery is charged when the apparatus is connected to an alternating power outlet.

OBJECTS OF THE INVENTION

A feature of the invention is that it results in an intermittent gas flow that results in reducing the high cost generally involved in supplying respiratory gases to patients as a continuous flow.

Another feature of the invention is, that as a result of intermittent gas flow, portable respiratory gas tanks can have their time of us extended.

Another feature of the invention is that the dose of respiratory gas is dependent on the spontaneous breathing pattern of the human patient or user. The spontaneous rhythmical act of breathing of a human is controlled by the special control centers in the human brain stem. The rate and depth of breathing are therefore controlled by the oxygen and carbon dioxide levels in arterial blood acting through a classical feedback loop and the dose will change due to the rate of breathing that can vary with sleep and exercising.

Methods of controlling the flow of gases of breathing apparatus by triggering a fixed dose of respiratory gas when inhalation takes place, can not adjust to the needs of a human patient or user whose breathing patterns are subject to spontaneous variations. A feature of the invention is that when used for oxygen therapy, the interrupted flow will be dependent on the human user's ventilating pattern and be similar in result with continuous flow that is also dependent on the human user's ventilating patterns. It, therefore, is possible to apply the clinical findings of continuous flow systems to this intermittent flow system because both are dependent on the human user's breathing patterns.

Another feature of the invention is that if a pneumatic breathing belt is used as the sensor, the human has the freedom of movement that will not affect the sensor due to body movements.

Another feature of the invention is that the patient or user has a choice of the sensor to be used; the one prong sensor detecting the negative pressure at the nostril can be used for day-time use when the human is fully aware if breathing is taking place through the nose.

The pneumatic breathing belt is the choice for night-time use, because breathing can be accomplished through the mouth during sleep, which cannot be sensed by the one-prong nasal sensor.

Another feature of the invention is that when the single prong nasal sensor is used, this breathing apparatus will indicate if the human is actually inhaling the respiratory gas.

An important feature of the invention is that the breathing apparatus can be built in a small size of light weight so a to be portable.

Another feature of the invention is that it can be used to provide oxygen concentrators with intermittent flow so that a greater flow of 90% oxygen can be achieved for higher flow rates than possible with a continuous flow system.

Another feature of the invention is that it can detect when the sensor is not working, or when the human has an apnea event (stops breathing), and emit a signal for intervention or help when these events occur.

Another feature of the invention is that it can be used with supplied air respirators to provide intermittent air flow for more efficient use of the air supply in industrial applications.

Still another feature of the invention is that a light emitting diode will signal when the battery requires recharging. Recharging takes place automatically each time the unit is operated by alternating current, or from a direct current source higher than the required operating direct current voltage.

BRIEF DESCRIPTION OF THE DRAWINGS

The foregoing and other objects, features, and advantages of the invention will be apparent from the following more particular description of preferred embodiments, as illustrated in the accompanying drawings in which reference characters refer to the same parts throughout the various views. The drawings are not necessarily to scale, emphasis instead being placed upon illustrating the principles of the invention.

DESCRIPTION OF THE PREFERRED EMBODIMENT

Figure 1:
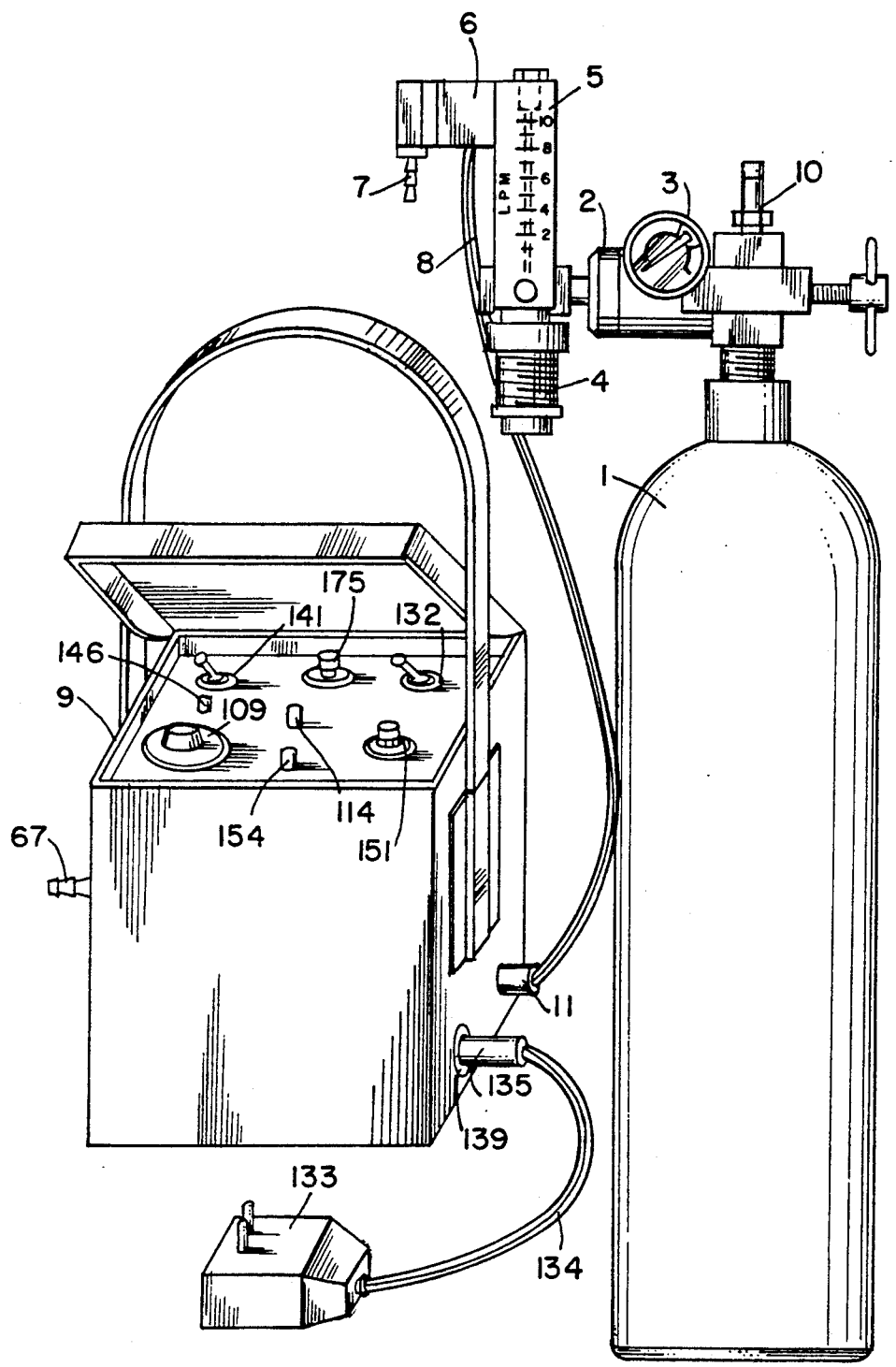
FIG. 1 is a diagrammatic view of an embodiment of the invention illustrative of the general disposition and arrangement of the apparatus in accordance with the invention shown in isometric projections.

FIG. 1 illustrates a breathing apparatus according to an embodiment of the invention which comprises a tank source of respiratory gas 1, a fixed pressure regulator 2, lowers the tank pressure of approximately 2,000 lbs. per square inch to a lower value (for example 20 to 50 pounds). A gauge 3 indicates the pressure of the gas in the tank 1. A second adjustable pressure regulator 4 is capable of zero pressure regulation and a flow meter 5 indicates the rate of flow of the gas. A normally open solenoid valve 6 is provided and a male barb connector 7 provides a means of connecting a cannula or mask to supply the respiratory gas to a human user or patient.

The masks and cannula are of the type used for oxygen therapy, such as a simple disposable mask, or a partial rebreathing mask, a non-rebreathing mask, or a venturi mask. The barb connector 7 can also be used for supplying respiratory air to hoods and respirators not shown for use where the atmosphere is dangerous to life or health. The normally open solenoid valve 6 is connected by means of an electrical cable 8 to a monitoring unit 9.

In use a valve 10 on tank 1 is open. Tank 1 pressure, in usual practice, has a filled pressure of 2,000 lbs. per square inch. The gauge 3 indicates the tank 1 pressure. The 2,000 lbs. per square inch pressure of the tank 1 is reduced to 20/50 lbs. per square inch by the fixed pressure regulator 2. If a fixed low pressure supply is available the fixed pressure regulator 2 is not required and the gas supply can be connected directly to the adjustable pressure regulator 4.

The adjustable pressure regulator 4 is used to adjust the rate of flow that is indicated by the flowmeter 5 to the required rate of respiratory gas flow required by the user or patient. The flowmeter 5 is connected to the solenoid valve 6 normally open and respiratory gas flows from barb connector 7. In use, the adjustable pressure regulator 4 is adjusted when no power is supplied to the valve 6 to the required rate of flow. The normally open valve 6 is used so that if a power failure occurs a continuous flow of respiratory gas is always available. The valve 6, when connected to an operating monitor 9, controls the flow of gas so that an intermittent flow results. The valve 6 and the flowmeter 5 can be connected to the output of an oxygen concentrator or other source of a constant stream of respiratory gas to achieve a higher rate of flow by means of intermittent gas flow than would be obtainable by continuous gas flow. An electric cable 8 is connected to the monitor 9 by means of a connector 11.

The supply of respiratory gas flowing from the barb 7 can be connected to a variety of masks, nasal cannulas, body tents, or hoods to supply respiratory gas to a patient or user. The supply of respiratory gas flowing from the barb 7 can be connected to one of nasal prongs 12 of a nasal cannula 13 of FIG. 2 to supply respiratory gas to the human user. The nasal cannula 13 is constructed so that one nostril of the nose receives a supply of intermittent gas flow from the nasal prong 12, while a nasal prong 14 is used to sense when breath inhalation takes place. A tube 15 connects prong 12 to the male barb connector 7 to receive the intermittent flow of gas from the source of respiratory gas.

A prong 14 is connected by a tubing 16 to an optoelectronic sensor 17. When the prong 14 is connected to a vacuum connection 18, the optoelectronic sensor 17 can signal either the time of inhalation or exhalation. The cannula 13 has a connecting plug 19 that prevents flow between the prongs 14 and 12 by blocking the opening at the connecting point of the tubes 16 and 15.

Figure 3:
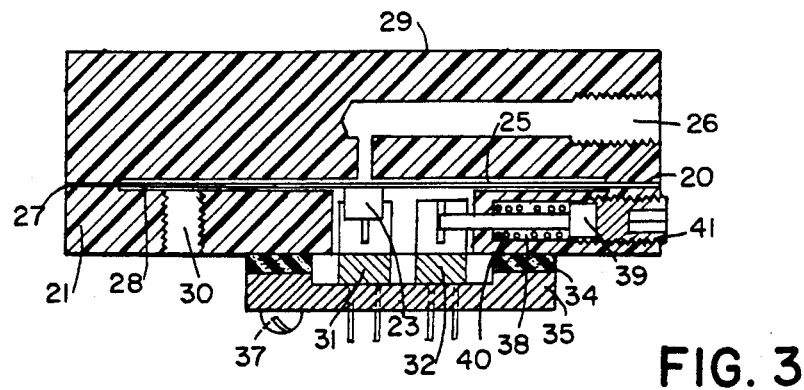
FIG. 3 is an enlarged sectional view taken along line 1—1 of FIG. 11.

The optoelectronic sensor 17 comprises a square housing 29 made of a rectangular opaque material shown in cross section in FIG. 3. The housing has a circular recess defining a central cavity 25 with a depth of 0.005" or more. An inlet connection 26 in the housing is in direct communication with the central cavity 25.

A sensing diaphragm 27 made of a 0.0005" thick polyester film or other suitable thin flexible material is pre-stressed circumferencially and bonded to a surface 20 of the square housing 29 thereby forming a space between the recessed central cavity 25 of the housing 29. This space changes when the diaphragm flexes when the human user of the apparatus inhales. It becomes larger when inhalation by the user takes place.

Figure 11:
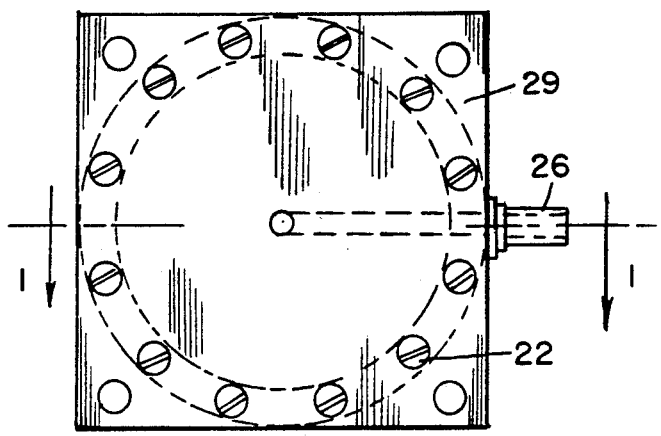
FIG. 11 is a top view of the optoelectronic sensor.
Figure 12:
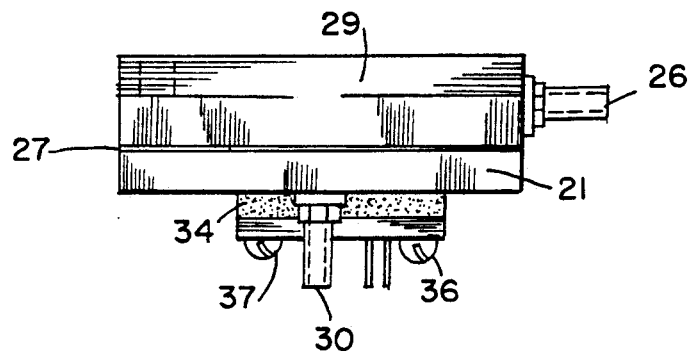
FIG. 12 is a front elevation view of the optoelectronic sensor.

A clamping disc 21, made of an opaque material, having a circular recess-forming central cavity 28 with a depth of 0.005" or more, is fastened to the square housing 29 by a plurality of screws 22, FIGS. 3 and 11.

The circular recess-forming upper central cavity 25 is vented to atmospheric pressure. The depth of the circular recess-forming central cavities 25 and 28 is kept to a minimum, being used to limit the movement of film diaphragm 27, to prevent film diaphragm 27 from being stretched by accidental over pressure.

The clamping disc 21 has an inlet connection 30 for the vacuum connection 18 that is in direct communication with the central cavity 28. In the center of the clamping disc 21 is disposed a rectangular opening to accept two optoelectronic solid state photon coupled interrupter modules 31 and 32. One module 31 is located in the center of the disc 21, and provides an electrical output when an infrared-opaque vane 23 is moved downward by the film diaphragm 27. The vane 23 is fastened to the center of the film diaphragm 27. A second module 32 is located as near as possible to the other module 31. The second module 32 is used as an inactive unit to provide a reference for temperature compensation.

Figure 13:
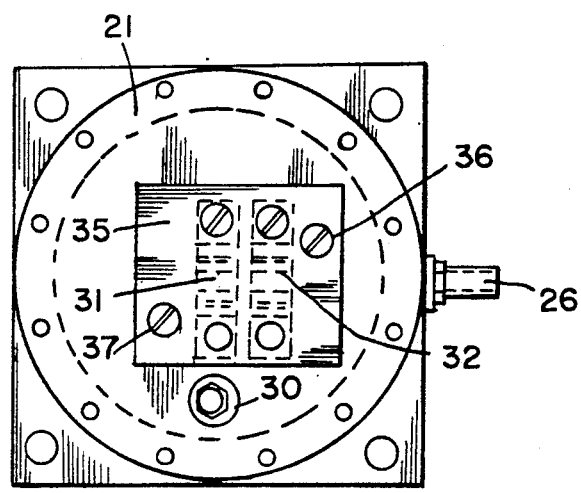
FIG. 13 is a bottom view of the optoelectronic sensor.

The modules 31 and 32 are mounted on a rectangular electrical non-conductor board 35 that has a gasketed spacer 34 made from neophrene cork sheet material that can be compressed by tightening the fastening screws 36 and 37, FIG. 13, to permit adjusting the distance that the two optoelectronic interrupter modules 31 and 32 can project into the clamping disc 21.

In the clamping disc 21 an internal chamber 38 is provided for a circular pin 39 that slides to adjust the electrical output of the optoelectronic interrupter module 32. The pin 39 is provided with a flange to allow a spring 40 to provide a constant pressure so a set screw 41 located in the threaded end of internal chamber 38 can regulate the distance that the pin 39 interrupts the module 32.

The electrical output of the module 31 is adjusted for maximum sensitivity to the sensing diaphragm 27 movement by tightening or loosening the fastening screws 36 and 37. After this is accomplished a set screw 41 is adjusted so the electrical output of the module 32 is the same as the output of the module 31.

Figure 4:
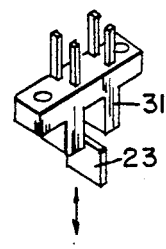
FIG. 4 is a perspective view of an optoelectronic interrupter module and infrared-opaque vane, according to the invention, in isometric projection.

FIG. 4 illustrates in an isometric view one of the optoelectronic modules (31 or 32) which are fastened to a board 35 by a plurality of screws 42, FIG. 13. The vane 23 is bonded to the center of the sensing diaphragm 27.

Figure 2:
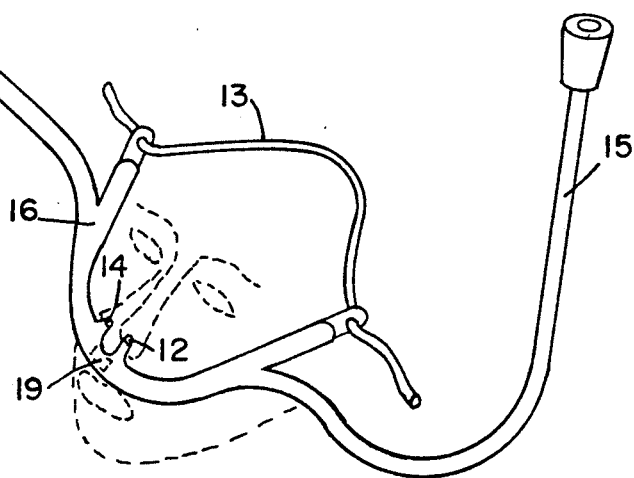
FIG. 2 is a diagrammatic view of a preferred form or embodiment of a two prong cannula worn by a human in isometric projection connected to an optoelectronic sensor that is a sectional view taken substantially along line 1—1 of FIG. 11.

FIG. 2 illustrates one of the ways that sensing of inhalation can be accomplished by the present invention. A second way of sensing inhalation is by using a pneumatic breathing belt sensor with minimum space maintaining tapes as shown in U.S. Pat. No. 4,602,643 of July 29, 1986. FIGS. 7, 8, 9, and 10 generally indicate a preferred embodiment of the invention which comprises an essentially rectangular shaped belt 45, FIG. 10, made of a flexible material such as sheet vinyl plastic or other suitable material having equivalent characteristics.

Figure 8:
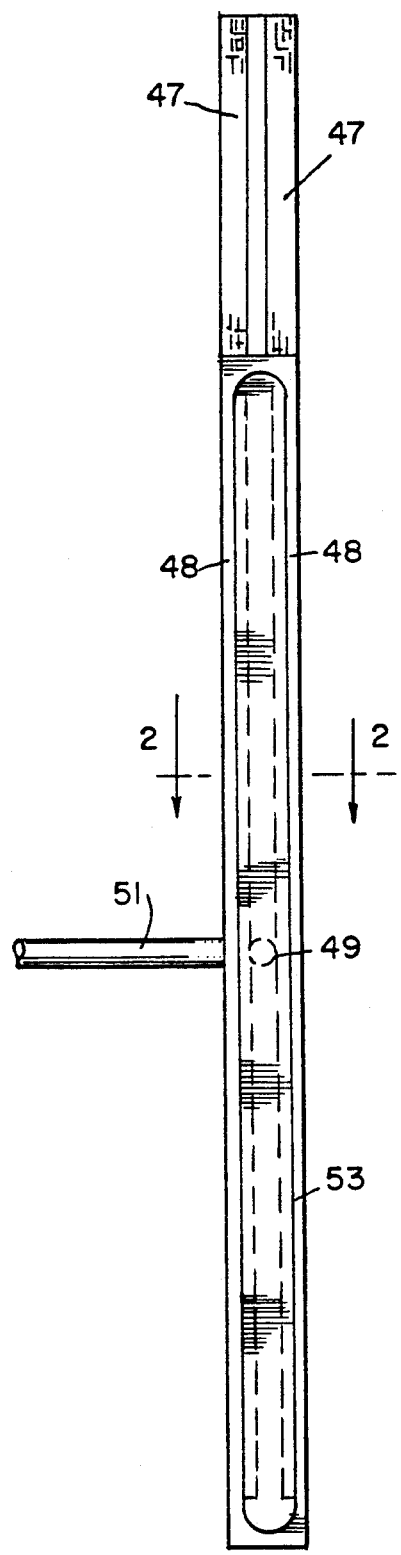
FIG. 8 is a front elevation view of the pneumatic breathing belt sensor.
Figure 9:
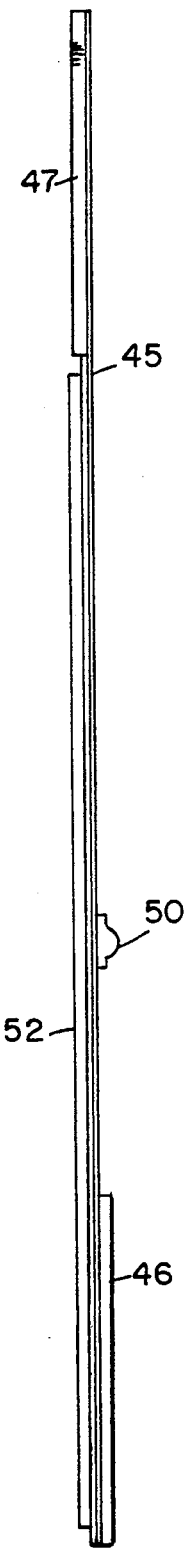
FIG. 9 is a side elevation view of the pneumatic breathing belt sensor.
Figure 10:
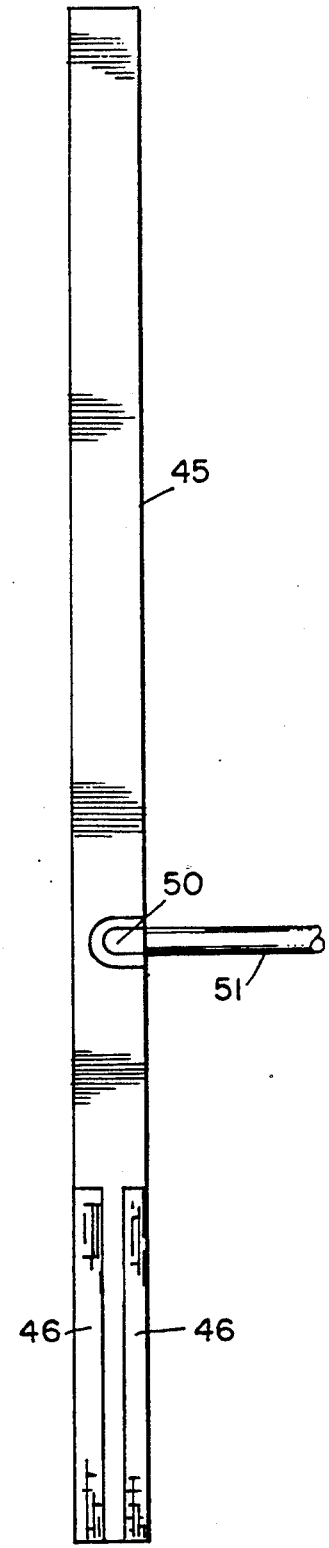
FIG. 10 is a rear elevation view of the pneumatic breathing belt sensor.

The belt 45, of flexible material, is provided with a means for fastening the two ends together and means for adjusting the size to meet the requirements of the user. FIGS. 8, 9, and 10 show a preferred embodiment where VELCRO (trademark Velcro U.S.A. Inc.) tape fastener is used for this purpose. VELCRO is a woven and molded hook and loop fastener. The woven and molded hook 46 consists of two tapes fastened to the belt 45 with adhesive or other suitable means of fastening at the extremity of one end of the belt. The extremity of the other end of the belt 45 on the opposite side, is provided with two tapes of woven and molded loops 47 fastened to the belt 45 with adhesive or other suitable means of fastening.

Figure 7:
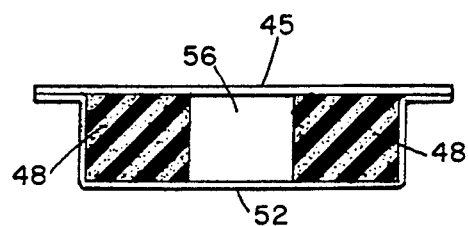
FIG. 7 is a sectional view taken along line 2—2 of FIG. 8.

A suitable elastic reaction in the form of a tape 48, essentially rectangular in cross section made of a foam material is fastened with adhesive to the belt 45 as shown in FIG. 7. The two tapes 48 are assembled by aligning on the belt 45 longitudinally as indicated by the dotted outline on FIG. 8. A vent hole 49 is provided in the belt 45 communicating with a molded plastic street elbow 50 fastened to the belt with adhesive, or other suitable means of fastening, for connecting a suitable flexible tube 51. The flexible tube 51 communicates with the vent hole 49. A very thin sheeting 52 is assembled over the tapes 48. The sheeting 52 can be a very thin sheet of vinyl or other suitable material. A preferred way of manufacturing is to have a rule type die made in a rectangular shape with round ends as shown by a line outline 53.

This die would be used with a high frequency or ultrasonic machine to make a heat seal between the belt 45 and the thin sheeting 52 following the unbroken circum-ambient relation of the outline 53 to effect a good fluid tight seal between the belt 45 and the thin sheeting 52. Sealing can also be accomplished with adhesive and the invention is not be to be limited to the heat or sonic sealing described.

Figure 6:
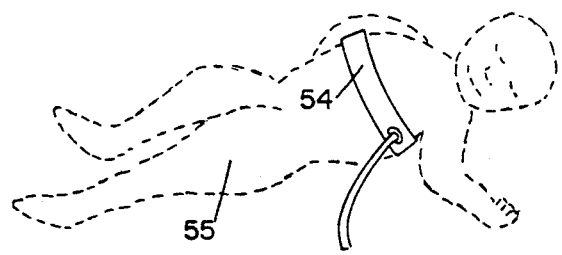
FIG. 6 is a perspective view of a human user with the pneumatic breathing belt sensor worn around the chest.

The assembly described is the pneumatic breathing sensor 54 around the chest of an infant 55 or adult as in FIG. 6 with the thin sheeting 52 next to the skin.

The pneumatic breathing sensor 54 is fitted loosely around the chest so that the elastic reaction tapes 48 are compressed when the chest is fully expanded as in deep inhaling. Exhaling results in the chest contracting, and the tapes 48 are then fully expanded. Air space 56 between tapes 48 is of larger volume when respiration air is being exhaled, and of smaller volume when respiration air is being inhaled. The action of inhaling and exhaling results in a flow of air in the tube 51, such that inhaling produces a positive flow (pressure) and exhaling produces a negative flow (vacuum).

When the pneumatic breathing sensor is worn around the midriff of a human user 55 at about the level of the diaphragm instead of around the chest, inhaling will produce a negative flow and exhaling will produce a positive flow.

The air space 56 is never completely closed since the tapes 48 always have some height when fully compressed and air can always reach the vent 49, when part of the tape is compressed by the weight of the body of the human 55.

Figure 5:
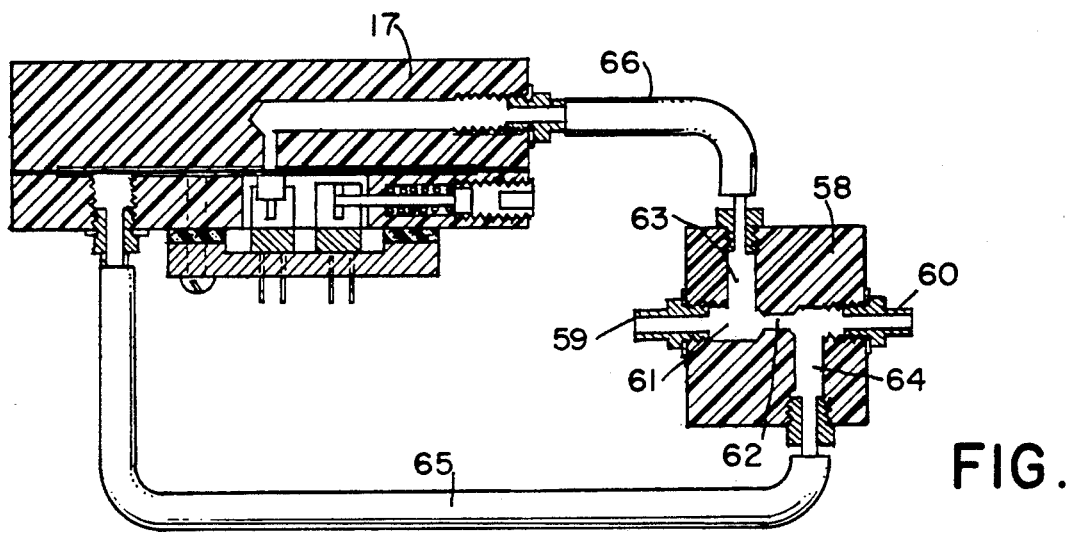
FIG. 5 is sectional view taken along line 1—1 of FIG. 11 with connections to a sectional view of a flow detector.

Tube 51 is connected to one of the ports 59 or 60 of a flow detector 58 of FIG. 5. The flow detector 58 is a preferred embodiment which comprises an essentially square block 58 with a transversely extending passageway 61 having a restrictive orifice 62 connecting the ports 59 and 60. The square block 58 has also a pair of transverse passageways 63 and 64 which communicate with passageway 61 and are positioned to measure the differential pressure created by the orifice 62 when air flows through the passageway 61. The differential pressure created by the air flow is used to actuate the optoelectronic sensor 17. The optoelectronic sensor 17 is connected to the flow detector 58 by tubings 65 and 66.

Humans wearing the pneumatic breathing sensor 54 around the chest when inhaling will create a positive flow (pressure) in the tube 51, FIG. 10, and a negative flow (vacuum) in the tube 51 when exhaling. The tube 51 can be connected to either port 59 or the port 60 of the flow detector 58. The port 60 is used to sense when exhalation is taking place by using the negative flow of air from the pneumatic breathing sensor 54 to create a negative differential pressure across the optoelectronic sensor 17. The optoelectronic sensor 17 can detect extremely low values of 0.001 of an ounce per square inch of differential pressure and can detect very low rates of flow in the passageway 61 created by exhaling. In like manner the port 59 can be used to detect inhalation.

The operation of the optoelectronic sensor 17 is identical when either prong 14 or the pneumatic breathing sensor 54 is used to detect breathing. The optoelectronic sensor 17 is as shown in the Dietz patent application "Optoelectronic Inhalation Sensor for Monitoring Inhalation and for Inhalation Therapy" Ser. No. 06/916,660 filed Oct. 6, 1986 and for which notice of allowance has been issued.

The flow of air from the tube 51 is always taking place when a human 55 is breathing and it is the function of the flow detector 58 to determine if it is a positive or negative flow; the volume of the flow can not affect this function. The pneumatic breathing sensor 54 is always vented to atmospheric pressure because one of the ports 59 or 60 is used for this purpose. If the user's body movements should compress the tapes 48 and create a random momentary high pressure or vacuum in the tube 51, port 59 or 60 will vent this and restore the output of the tube 51 to its normal function of determining the direction of flow by detecting a pressure or vacuum.

In use, the tube 51 of the pneumatic breathing belt 54 is connected to the inlet connection 67 of the monitor 9. The inlet connection 67 is connected to the flow detector 58 at the port 59 to sense inhalation or connected to the port 60 to sense exhalation.

Figure 14:
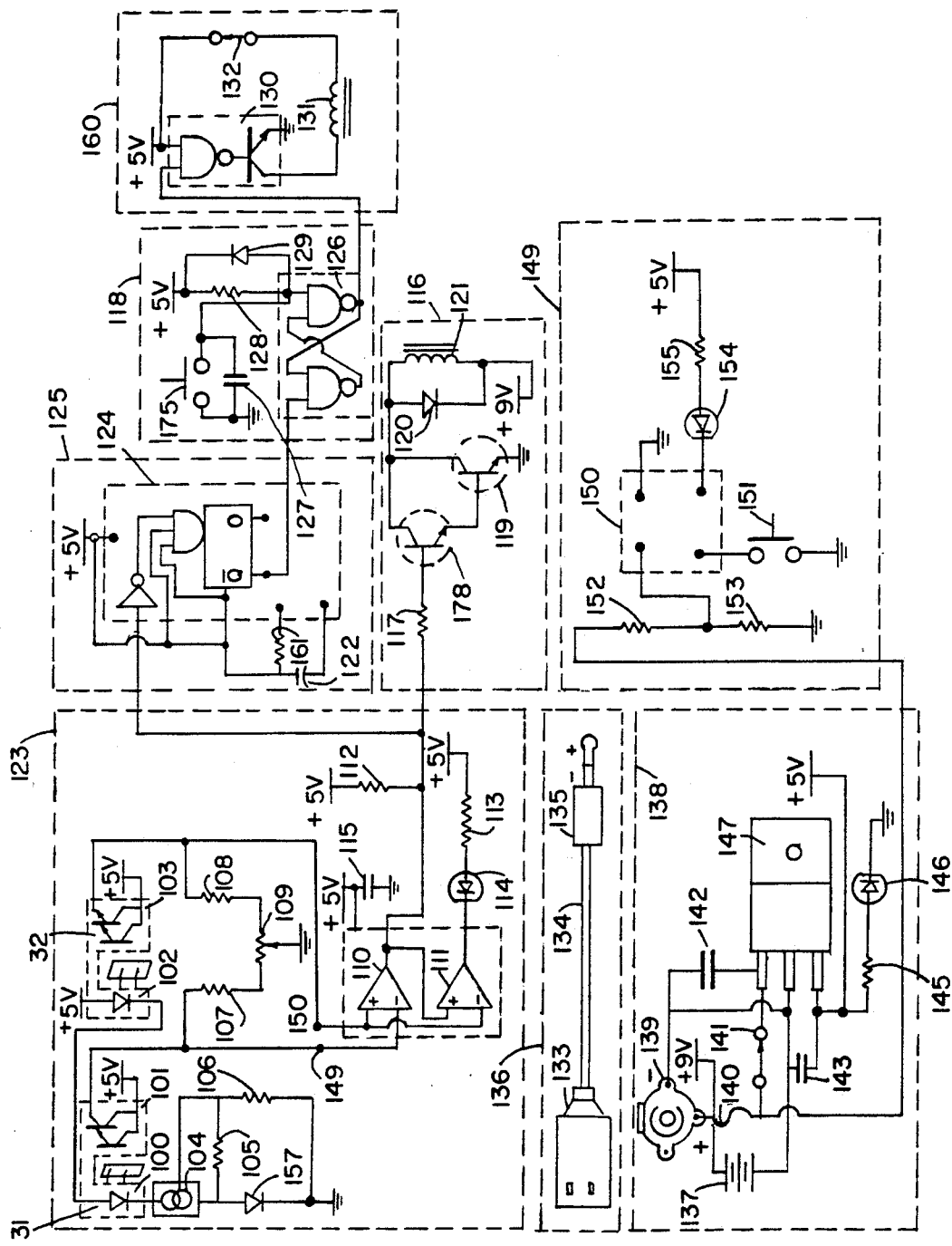
FIG. 14 is a schematic diagram of electrical circuits in accordance with the invention.

The flow of air through the passageway 61 will create a differential pressure across the optoelectronic sensor 17 which will cause movement of the sensing diaphragm 27. The movement of the diaphragm 27 will result in the infrared-opaque vane 23 interrupting the infrared light beam emitting from a gallium arsenide diode 100, FIG. 14, which is normally coupled to a silicon darlington connected phototransistor 101, which is housed in a solid state photon coupled interrupter module 31.

The interrupter module 31 is mechanically adjusted for peak electrical output by tightening or loosening the screws 36 and 37.

The second solid state photon coupled interrupter module 32 is used for temperature compensation to balance the temperature changes of the other module 31. Movement of the adjusting screw 41 will result in interrupting the infrared light beam emitting from the gallium arsenide diode 102 of FIG. 14, which is normally coupled to a silicon darlington connected phototransistor 103, FIG. 14, which is housed in the solid state photon coupled interrupter module 32.

The interrupter module 32 is mechanically adjusted for an electrical output equal to that of the electrical output of the other module 31 by adjusting screw 41.

The outputs of diodes 100 and 102 are made to have consistent infrared emitted light output over a wide temperature range by connecting the diodes in series and supplying them with a constant fixed current by use of a three terminal adjustable current source 104 that has a zero temperature coefficient established by using resistors 105 and 106 with diode 157.

The outputs of the module 31 and the module 32 are connected to resistors 107 and 108 respectively which are connected to an adjusting potentiometer 109 which has its movable tap connected to ground. The potentiometer 109 is adjusted to obtain maximum sensitivity of the optoelectronic sensor 17. The potentiometer 109 is located on a control panel of monitor 9, FIG. 1.

The electrical output of the module 31 is fed into the inverting input of voltage comparator 110. The electrical output of the module 32 is fed into the non-inverting input of a voltage comparator 110.

The voltage output of the comparator 110 is fed into a non-inverting input of a comparator 111. A reference voltage is obtained from the output of a silicon darlington connected phototransistor 103 which is fed into the inverting input of the comparator 111.

The output voltages of comparators 110 and 111 will swing from full ON to full OFF when the voltages applied to the inputs differ by about 0.001 volt. Thus a very small movement of vane 23 will produce a very small voltage change that will result in the output of the comparators 110 and 111 swinging from full OFF to full ON with the voltage being applied to output resistors 112 and 113. A light emitting diode 114 will be illuminated each time the user exhales, and extinguished each time the user inhales. A capacitor 115 is used in the circuit to remove power supply spikes.

The output of the comparator 110 is fed to a circuit layout 116 that is used to energize a normally open gas supply valve 6. This is accomplished by feeding the output of the comparator 110 to a resistor 117 which is connected to the base of a transistor 178. The emitter of the transistor 178 is connected to the base of a transistor 119 and the collector of the transistor 178 is connected to the collector of the transistor 119. The emitter of the transistor 119 is connected to ground. The common collector connection of the transistors 178 and 119 is connected to a coil 121 of the normally open solenoid valve 6. A diode 120 protects the transistors 178 and 119 from the voltage produced in the coil 121 of the solenoid valve 9. When a voltage output of the voltage comparator 110 is applied to the resistor 117, it results in a current flowing through the transistors 178 and 119 that energizes the coil 121 of the solenoid valve 9.

A circuit 123 which detects either exhalation or inhalation by sending an electrical signal to the circuit 116 that energizes the solenoid valve 9 is used to supply a respiratory gas for the length of time that inhalation is taking place.

The output of the voltage comparator 110 is also fed to a circuit layout 125 that is a missing pulse detector. This circuit is a one-shot timer that is continually retriggered by incoming pulses each time the user inhales. A missing or delayed pulse, that occurs whenever a user fails to inhale for a preset time or stops breathing, will prevent retriggering before a timing cycle is completed, and results in a signal being sent to alarm circuits 118 and 160. The missing pulse circuit 125 consists of an integrated timer circuit on a silicon chip 124 with a capacitor 122 and resistor 161 of the correct values to obtain the maximum length of time between inhalation that will result in an alarm signal being sent to alarm circuits 118 and 160.

The circuit 118 is a latching circuit that is used to cause a continuous alarm to be sounded when a missing pulse created by too great a length of time between inhalations or lack of breathing occurs. A monitary switch 175, located on the control panel of monitor 9 of FIG. 1 is used to reset the latching circuit to shut off the alarm, which is activated again if too great a length of time between inhalations or lack of breathing occurs. The circuit 118 consists of a two input nand gate integrated chip 126, a capacitor 127, a resistor 128, and a diode 129. The latching circuit 118 sends a continuous alarm signal, once it is activated, to circuit 160 which is used to energize a piezo electric buzzer 131.

The circuit 160 consists of a dual peripheral driver interface integrated circuit chip 130, the piezo electric buzzer 131, and a switch 132.

An alarm signal from latching circuit 118 will send an input into the chip 130 which will cause a current to flow energizing the piezo electric buzzer 131. The switch 132 located on the control panel of the monitor 9 is used to deactivate the alarm signal. The Buzzer 131 is located internally in the monitor 9.

A wall transformer 136, consists of a transformer 133 that reduces the 110 volts alternating current of wall outlets to a lower voltage, such as 9 volts direct current, a connecting cable 134, and a connecting plug 135. Connecting plug 135 allows monitor 9 to be operated from 110 volts and provides a charging voltage for a battery 137.

A circuit 138 is a power supply that normally is supplied with power from the battery 137, or with power from the wall transformer 136 obtained by plugging connector 135 into a jack 139 located on the side of monitor 9.

An on/off power switch 141 located on the control panel of monitor 9 is used to turn monitor 9 OFF and ON. A light emitting diode 146 emits light when power is flowing in a resistor 145 and is located on the control panel of monitor 9.

Power that is supplied either by the wall transformer 136, or by the battery 137 is applied to the input terminals of a voltage regulator 147. The input voltage of approximately 9 volts direct current is then regulated to a fixed voltage of 5 volts direct current. A capacitor 142 connected to an input terminal of a voltage regulator 147 is used to trap spikes that may arise from the wall transformer 136 electrical output. The capacitor 143 connected to the output terminal of the voltage regulator 147 is used to trap spikes that bother the integrated circuits being used. A fuse 140 prevents damage if some malfunction should occur that would cause an excessive current to flow.

A circuit 149 is used for indicating a low battery voltage and consists of a low battery voltage indicator integrated circuit chip 150, a voltage divider consisting of resistors 152 and 153, a switch 151 that is used to test light emitting diode 154, and a resistor 155. The switch 151 and the light emitting diode 154 are located on the front panel of the monitor 9. A voltage divider consisting of resistors 152 and 153 is used to lower the supply voltage to some voltage such as 2.9 volts. A light emitting diode 154 will light at voltages below 2.9 volts; at voltages above 2.9 volts the light emitting diode 154 may be lit by activating the switch 151. The light emitting diode 154 indicates when the battery 137 has become depleted so that the voltage divider tap is 2.9 volts or less and indicates that the battery 137 needs to be recharged. Recharging of the battery 137 is accomplished by plugging the wall transformer 136 into a 110 volt alternating current outlet.

All the circuits 123, 125, 118, 160, 116, 138, and 149 are located internally in the monitor 9.

In use the pneumatic breathing belt 54 is placed around the user's upper chest to indicate when the user 55 is inhaling. The belt's two ends are then fastened together by means of VELCRO tape fasteners loosely around the chest. When the user 55 inhales, the elastic reaction in the form of the tapes 48, is compressed reducing the air space 56. This results in a positive flow of air in the tube 51 connected to the airflow detector 58. The flow of air produces a differential air pressure that actuates the optoelectronic sensor 17. The optoelectronic sensor 17 can be adjusted for maximum sensitivity by adjusting potentiometer 109 of circuit 123. The optoelectronic sensor 17 may be located on the same printed circuit board that mounts circuit 123, 125, 118, 160, 116, 138, and 149 which are housed internally in the monitor 9.

When the optoelectronic sensor 17 is activated by the human user 55 inhaling, the normally open solenoid valve 6 is de-energized allowing a flow of respiratory gas to flow for the length of time the human user 55 is inhaling.

Everytime the human user 55 exhales, the solenoid valve 6 is energized and the flow of gas is cut off. Since normal inhalation is approximately 30% of the breathing cycle, there can be a saving of approximately 70% of the respiratory gas.

The amount of gas supplied to the human user 55 is a function of the human's spontaneous demand that determines the rate and depth of breathing. The rate and depth of breathing are principally controlled by the oxygen and carbon dioxide levels in the arterial blood acting through a classical feedback loop that is controlled by the special control center in the human brain stem.

The monitor 9 can detect when apnea (the absence of breathing) occurs or if the pneumatic breathing belt 54 does not function. This is accomplished by the missing pulse detector circuit 125. If an inhalation pulse is not received within a pre-determined fixed time period, the piezo electric buzzer alarm 131 will sound. This alarm 131 will be energized and can only be de-energized by closing the alarm reset switch 175. If desired, this alarm can be made non-operative by placing the switch 132 in the OFF position.

The monitor 9 is operated either from its internal rechargeable battery 137 or from a 110 volt alternating current outlet.

If the battery 137 becomes depleted, the light emitting diode 154 will light indicating recharging is necessary. Recharging is accomplished by simply using the wall transformer 136. The light emitting diode 154 can be tested for function by pressing the switch 151, which will light the light emitting diode 154 if found satisfactory.

The monitor 9 can be used with the pneumatic breathing belt 54, or with the special nasal cannula shown in FIG. 2. The pneumatic breathing belt 54 will always work and is recommended for night-time use. The nasal cannula has the disadvantage of necessitating that the human user not breath through his mouth, as it will function only when nasal breathing is taking place. Therefore, it is recommended only for use where the human user is aware that he is breathing through his nose and does not want the inconvenience of the belt 54 around his chest.

The respiratory gas supply flowing from outlet 7 can be connected to any number of masks that are well-known in the art of respiratory health care and industrial respirators. Since the sensing devices are completely separate from the respiratory gas supply, humidity can be administered with the gas supply with no harmful effects to the sensing devices.

Figure 15:
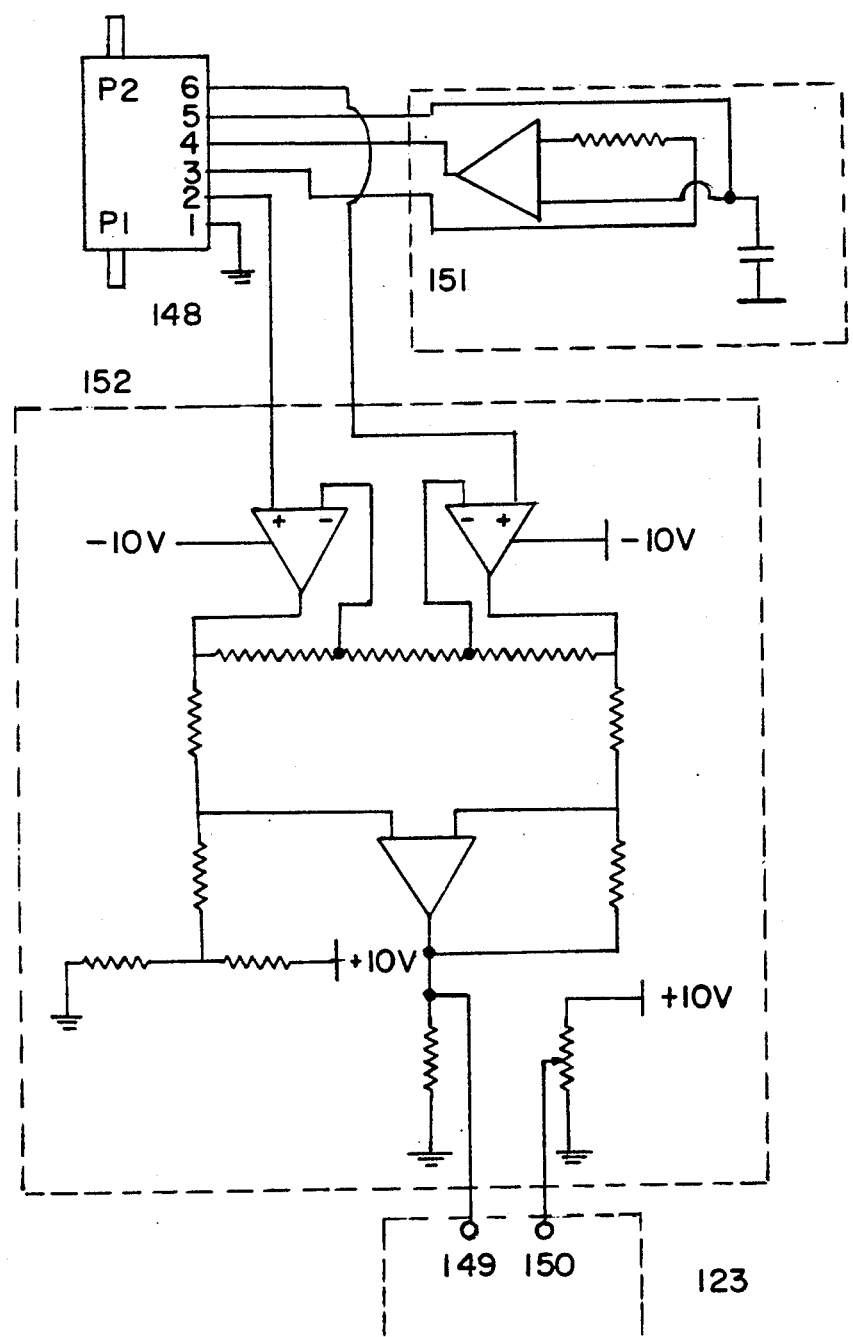
FIG. 15 is a schematic drawing of the electrical circuit of a second embodiment of the invention using a flow switch in accordance with the invention.

A second embodiment of the invention using a flow sensor 148, FIG. 15, such as the Microbridge Airflow Sensor manufactured by Micro Switch, can be used in place of the optoelectronic sensor 17 and flow detector 58 of FIG. 5.

If the flow sensor 148 is used with the one prong 14 of the two prong cannula of FIG. 2 for sensing inhalation, the tube 16 is connected to the flow sensor 148 instead of the optoelectronic sensor 17.

In like manner, the flow sensor 148 can be connected to the tube 51 of the pneumatic breathing belt sensor 54 instead of the flow detector 58 of FIG. 5 to sense inhalation or exhalation.

The flow sensor 148 requires a heater control circuit 151 and an instrumentation amplifier 152 for operation. To use the flow sensor 148 it is necessary to disconnect the optoelectronic sensor 17 at points 149 and 150 of FIG. 14 and reconnect flow sensor 148 to points 149 and 150 of FIG. 15.

The operation of the heater control circuits and instrumenation amplifiers is well-known in the art and consequently has been diagrammatically illustrated and no further description thereof is given other than as required to thoroughly illustrate that the flow switch 148 can be used in place of the optoelectronic sensor 17 in the present invention.

While the invention has been particularly shown and described with references to the preferred embodiments thereof, it will be understood by those skilled in the art that various alterations in form and detail may be made therein without departing from the spirit and scope of the invention. Moreover, while the invention has been particularly shown and described for clinical use, it should be understood that the invention may be used in conjunction with gas supply or apnea detection in a subject in industrial, aeronautical, subterranean or underwater environments.

I claim:

1. A method for supplying respiratory gas to a human user for the length of time that the human user inhales, where the act of the inhalation is detected by a single optoelectronic sensor means that can detect the inhalation by a nasal cannula when breathing takes place through the human's nose and by a pneumatic belt when breathing takes place through the human's mouth, comprising the steps of:

detecting the inhalation by the human, wherein said step of detecting is carried out with the optoelectronic sensor means detecting the inhalation by a first pressure from the nasal cannula when the breathing takes place through the human's nose and by a second pressure from the pneumatic belt when breathing takes place through the human's mouth;

generating a first electrical signal wherein said step of generating is carried out with the optoelectronic sensor means generating the electrical signal activated by the first pressure from the nasal cannula;

generating the electrical signal activated by the second pressure from the pneumatic belt;

applying said first electrical signal to generate a second electrical signal wherein said step of generating the second electrical signal is carried out by a monitoring means for generating the second electrical signal whenever the first electrical signal is received;

applying the second electrical signal to supply a flow of the respiratory gas wherein said step of supplying the respiratory gas is carried out by a valve means controlled by the second electrical signal.

2. The method of claim 1 whereby the first electrical signal actuates an auditory alarm when inhalation failure occurs, wherein said step of the auditory alarm is carried out with a missing pulse detector means, whereby the first electrical signal activates the missing pulse detector means for each time the inhalation takes plate; failure for the inhalation to take place results in actuating the auditory alarm when the first electrical signal pulse is missed.

3. A method for supplying supplemental oxygen for day and night respiratory therapy, comprising the steps of:

providing a nasal cannula
   detecting inhalation at the nasal cavities, wherein said step of detecting inhalation is carried out with the nasal cannula for daytime use;
   providing a pneumatic belt
   detecting inhalation by chest movement, wherein said step of detecting inhalation is carried out with the pneumatic belt for nighttime use;
   supplying supplemental oxygen when the inhalation is detected; wherein said step of supplying supplemental oxygen is carried out with a monitor means that supplies oxygen to a human each time the inhalation is detected at the nasal cavities or each time the inhalation is detected by the chest movement.

4. The method as defined by claim 3, wherein said step of detecting inhalation is carried out by optoelectronic sensor means detecting inhalation by the nasal cannula or chest movement.

5. The method as defined by claim 3, wherein said step of detecting inhalation is carried out by flow sensor means detecting inhalation by the nasal cannula or chest movement.

6. The method as defined by claim 3, detecting inhalation failure actuates an auditory alarm, wherein said step detecting inhalation failure is carried out with the missing pulse detector means.

7. An improved breathing apparatus having a source of respiratory gas wherein the use of a single optoelectronic sensing means in combination with a nasal cannula and a pneumatic belt, provides for supplying the respiratory gas day and night to a human user for the length of time the human user inhales, in combination:

the nasal cannula, for detecting inhalation and for delivering a supply of oxygen, wherein the dual function is carried out each time the human inhales;
   the pneumatic belt, for detecting inhalation, wherein movement of the chest provides an equivalent means of detecting the inhalation;
   the optoelectronic sensor, that detects inhalation from the nasal cannula or the pneumatic belt and actuates a first electrical signal, for the length of time the human inhales;

a monitor for supplying a second electrical signal activated by the first electrical signal from the optoelectronic sensor;

a valve coupled to the source of respiratory gas activated by the second electrical signal from the monitor controlling the supply of respiratory gas supplied to the nasal cannula for the length of time the human user inhales.

8. An improved breathing apparatus according to claim 7; in further combination:

a missing pulse detector activated by the first electrical signal from the optoelectronic sensor;

an auditory alarm actuated by the missing pulse detector to signal the failure of inhalation.

9. An improved breathing apparatus according to claim 7; in further combination:

two solid photon coupled interrupter modules, in which the first module detects inhalation, and the second module provides temperature compensation for the optoelectronic sensor;

a three terminal adjustable current source to supply a constant fixed current having a zero temperature coefficient to the optoelectronic sensor, to provide additional temperature compensation.

10. An improved breathing apparatus having a source of respiratory gas wherein the use of a single flow sensing means in combination with a nasal cannula and a pneumatic belt, provides for supplying the respiratory gas day and night to a human user for the length of time the human user inhales, in combination:

the nasal cannula, for detecting inhalation and for delivering a supply of oxygen, wherein the dual function is carried out each time the human inhales;

the pneumatic belt, for detecting inhalation, wherein movement of the chest provides an equivalent means of detecting the inhalation;

the flow sensor, that detects inhalation from the nasal cannula or the pneumatic belt and actuates a first electrical signal, for the length of time the human inhales;

a monitor for supplying a second electrical signal activated by the first electrical signal from the flow sensor;

a valve coupled to the source of respiratory gas activated by the second electrical signal from the monitor controlling the supply of respiratory gas supplied to the nasal cannula for the length of time the human user inhales.

* * * * *